US011819679B2

(12) United States Patent
Jurna et al.

(10) Patent No.: US 11,819,679 B2
(45) Date of Patent: Nov. 21, 2023

(54) CENTROSYMMETRIC RADIO FREQUENCY ELECTRODE CONFIGURATION FOR SKIN TREATMENT

(71) Applicant: KONINKLIJKE PHILIPS N.V., Eindhoven (NL)

(72) Inventors: Martin Jurna, Eindhoven (NL); Jonathan Alambra Palero, Eindhoven (NL); Marco Baragona, Eindhoven (NL); Margaret Ruth Horton, Eindhoven (NL); Babu Varghese, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 916 days.

(21) Appl. No.: 15/314,993

(22) PCT Filed: Jun. 3, 2015

(86) PCT No.: PCT/EP2015/062313
§ 371 (c)(1),
(2) Date: Nov. 30, 2016

(87) PCT Pub. No.: WO2015/185583
PCT Pub. Date: Dec. 10, 2015

(65) Prior Publication Data
US 2017/0189668 A1    Jul. 6, 2017

(30) Foreign Application Priority Data

Jun. 4, 2014    (EP) ..................................... 14171193

(51) Int. Cl.
*A61N 1/00*    (2006.01)
*A61N 1/40*    (2006.01)
(Continued)

(52) U.S. Cl.
CPC ................ *A61N 1/00* (2013.01); *A61B 18/14* (2013.01); *A61N 1/0476* (2013.01); *A61N 1/18* (2013.01);
(Continued)

(58) Field of Classification Search
CPC . A61N 1/18; A61N 1/403; A61N 1/00; A61N 1/0476; A61N 1/328; A61B 18/14; A61B 2018/0047
(Continued)

(56) References Cited

U.S. PATENT DOCUMENTS 6,228,078 B1 *    5/2001    Eggers ................... A61B 18/12
                                                            604/114
6,413,255 B1 *    7/2002    Stern ....................... A61B 18/14
                                                            606/41
(Continued)

FOREIGN PATENT DOCUMENTS

DE    102011053731 A1    3/2013
KR    101227224 B1    1/2013
(Continued)

*Primary Examiner* — Joseph A Stoklosa
*Assistant Examiner* — Adam J Avigan (57) ABSTRACT

A device for RF skin treatment includes an outer electrode arranged on an operational side of the device. The outer electrode has an annular or equilateral polygonal shape. An inner electrode is arranged at a center of the outer electrode and is surrounded by the outer electrode. An RF generator is arranged to supply an RF treatment voltage between the inner electrode and the outer electrode. A skin contact surface of the inner electrode has a largest cross-sectional dimension in a range of 200-500 μm, and the RF treatment voltage is less than 50 V.

19 Claims, 7 Drawing Sheets

(51) Int. Cl.
  *A61N 1/04* (2006.01)
  *A61N 1/32* (2006.01)
  *A61B 18/14* (2006.01)
  *A61N 1/18* (2006.01)
  *A61B 18/00* (2006.01)

(52) U.S. Cl.
  CPC ............. *A61N 1/328* (2013.01); *A61N 1/403* (2013.01); *A61B 2018/0047* (2013.01)

(58) Field of Classification Search
  USPC ........................................................... 607/101
  See application file for complete search history.

(56) References Cited

U.S. PATENT DOCUMENTS

| | | | | |
|---|---|---|---|---|
| 2004/0002746 A1* | 1/2004 | Ryan | ...................... | A61B 18/14 607/99 |
| 2004/0019371 A1* | 1/2004 | Jaafar | ................... | A61N 1/325 607/50 |
| 2007/0206986 A1* | 9/2007 | Gueret | ................... | A45D 34/04 401/123 |
| 2008/0183167 A1 | 7/2008 | Britva | | |
| 2008/0183251 A1* | 7/2008 | Azar | ...................... | A61B 18/18 607/101 |
| 2010/0010480 A1* | 1/2010 | Mehta | ................... | A61B 18/14 606/9 |
| 2010/0016849 A1* | 1/2010 | Rosenberg | ............... | A61N 7/00 606/41 |
| 2011/0009860 A1* | 1/2011 | Chornenky | ............ | A61B 18/14 606/41 |
| 2011/0015625 A1* | 1/2011 | Adanny | ............. | A61B 18/1233 606/33 |
| 2012/0185029 A1* | 7/2012 | Flyash | ................... | A61B 18/14 607/148 |
| 2013/0079766 A1* | 3/2013 | Adanny | ................. | A61B 18/14 606/33 |
| 2013/0226269 A1* | 8/2013 | Eckhouse | ............ | A61N 1/0496 607/88 |
| 2013/0289679 A1* | 10/2013 | Eckhouse | ............ | A61N 1/403 607/102 |
| 2014/0005658 A1* | 1/2014 | Rosenbegr | ............ | A61B 18/18 606/33 |
| 2014/0207217 A1* | 7/2014 | Lischinsky | ........ | A61N 1/36014 607/102 |
| 2017/0189704 A1* | 7/2017 | Palero | ...................... | A61N 1/40 |
| 2017/0202606 A1* | 7/2017 | Horton | ............. | A61B 18/1206 |
| 2018/0110977 A1* | 4/2018 | Palero | ................... | A61B 18/14 |
| 2018/0207421 A1* | 7/2018 | Jurna | ...................... | A61B 18/14 |

FOREIGN PATENT DOCUMENTS

| | | |
|---|---|---|
| WO | 2012023129 A1 | 2/2012 |
| WO | 2012052986 A2 | 4/2012 |
| WO | 20140207217 A1 | 7/2014 |

* cited by examiner

CENTROSYMMETRIC RADIO FREQUENCY ELECTRODE CONFIGURATION FOR SKIN TREATMENT

This application is the U.S. National Phase application under 35 U.S.C. § 371 of International Application No. PCT/EP2015/062313, filed on Jun. 3, 2015, which claims the benefit of European Application No. 14171193.7 filed on Jun. 4, 2014. These applications are hereby incorporated by reference herein.

FIELD OF THE INVENTION

The invention relates a device for skin treatment, in particular for radio frequency (RF) treatment of human skin. The device is primarily suitable for skin tightening and/or skin rejuvenation, in particular for fractional RF skin treatment. The invention also relates to the use of such a device for skin treatment.

BACKGROUND OF THE INVENTION

Radio frequency (RF) is conventionally used in both the professional and home-use aesthetic market for skin tightening. The ability to heat a large volume at dermal skin level has made the radio frequency technology the standard for skin tightening and for treating skin laxity. Compared to laser treatments, RF devices have a relatively lower cost price and can provide larger-volume and deeper tissue contraction. Additionally, RF energy dissipation does not rely on absorption of light by chromophores, so that tissue pigmentation or the vascular network does not interfere with the delivery of energy.

The basic principle of RF energy delivery at the skin surface and from there to tissue is that an alternating current is applied in a closed circuit with the skin. Tissue impedance directly affects the extent of the heating: RF propagates more easily through tissues with high conductivity (low electrical resistance), while tissues with high electrical resistance (high impedance, low conductance) are poor conductors of RF energy. RF energy takes the path of least resistance through skin tissue and is dissipated as thermal energy primarily due to molecular vibrations.

A growing application for RF beyond skin tightening is skin rejuvenation. In most RF skin rejuvenation devices, fractional thermal lesions in the skin are created simultaneously using small electrodes. Recently different professional devices have been launched onto the aesthetic market to address skin rejuvenation with a radio frequency device. Skin rejuvenation is a combination of different consumer benefits such as: even skin tone, reduction of pigmentation spots, improved radiance and texture and reduction of fine lines. Here the energy is used primarily to damage the stratum corneum and the epidermis (including the dermal-epidermal junction) and possibly the top part of the dermis. Traditionally, skin rejuvenation treatments are done by ablative or non-ablative settings of a laser wavelength highly absorbed by water, whereby the ablative treatments vaporize the skin and create hollow pillars in the skin and the non-ablative treatments heat the skin to 65-100° C. to initiate cell necrosis, collagen denaturation and contraction, and eventually collagen remodeling.

To date, fractional skin treatments using RF are limited to professional use. One possible reason is the safety of the treatment to ensure that the RF heating does not result in ablative damage to the skin tissue. This is particularly challenging since the amount of RF energy deposited in the tissue depends on local tissue impedance, and skin tissues have inhomogeneous impedance distribution. This uncertainty in impedance combined with the use of high current densities and voltages results in uncertainty in achieved temperatures in skin tissues during treatment, resulting in the occurrence of both non-ablative thermal lesions and the undesirable ablative tissue damages.

Patent application WO 2012/023129 describes an apparatus for personal aesthetic skin treatment by RF voltage. The apparatus includes an assembly of individual electrodes operative to contact fractions of the skin and deliver RF treatment voltage to each fraction. In a test mode of the apparatus, a test voltage is applied to the electrodes enabling determination of the quality of the contact between each of the electrodes and the skin. In the test mode no thermal lesions are generated in the skin. In a treatment mode, following the test mode, a treatment voltage is applied to generate thermal lesions in the skin. The test voltage does not exceed 50 Volt. The applied treatment voltage has higher values which lie between 50 Volt and 400 Volt.

SUMMARY OF THE INVENTION

It is an object of the invention to provide a device for RF skin treatment with improved safety in that it enables the generation of non-ablative fractionated skin lesions particularly by using a lower RF treatment voltage as compared to known devices, so that a feedback or monitoring system to detect proper contact between the electrodes and the skin is not required. For this purpose, according to a first aspect of the invention, a device for RF skin treatment is provided comprising an outer electrode arranged on an operational side of the device and having an annular or equilateral polygonal shape. The device comprises an inner electrode arranged on the operational side of the device at a center of the outer electrode and surrounded by the outer electrode. An RF generator is arranged to supply an RF treatment voltage between the inner electrode and the outer electrode. A skin contact surface of the inner electrode has a largest cross-sectional dimension in a range of 200-500 µm, and the RF treatment voltage is less than 50 V. In an embodiment, the skin contact surface of the inner electrode is circular. In this embodiment, the largest cross-sectional dimension of the skin contact surface corresponds to a diameter of the skin contact surface and is in said range of 200-500 µm. The circular inner electrode may be annular (i.e. ring shaped) or disc shaped (i.e. having the shape of a filled circle). The inner electrode may also be non-circular, for example square-shaped, having a largest cross-sectional dimension within the range as mentioned above.

The proposed range of the largest cross-sectional dimension of the skin contact surface of the inner electrode of 200-500 µm enables, in combination with a relatively low treatment voltage of below 50 Volts, the generation of thermal lesions that are large enough for effective skin rejuvenation and small enough to enable fast recovery of the skin.

The inner and outer electrodes are configured to simultaneously make contact to the skin. The actual skin contact surface of the inner electrode does not need to be flat. It may be curved. This also applies to the actual skin contact surface of the outer electrode. In this respect, when the skin contact surface is flat, the expression "a largest cross-sectional dimension of the skin contact surface" refers to a largest dimension of the skin contact surface measured in the plane of the skin contact surface. When the skin contact surface is not flat, in particular when it is curved, the expression "a largest cross-sectional dimension of the skin contact surface" refers to a largest dimension measured in a cross-section of the inner electrode containing the outer circumference of the skin contact surface.

In an embodiment, the largest cross-sectional dimension of the skin contact surface of the inner electrode is in a range of 200-400 µm. Values for the largest cross-sectional dimension of the skin contact surface of the inner electrode within this preferred range have shown good results in ex-vivo skin tests.

In an embodiment, the RF treatment voltage is 40 V or less, such as 39 V. The above mentioned values for the largest cross-sectional dimension of the skin contact surface of the inner electrode enable sufficient warming of the skin, even with relatively low treatment voltages. It should be noted that the treatment voltage should not be too low, because in order to create lesions a sufficient amount of energy is required. Preferably the RF treatment voltage should not be lower than 20 volts when the RF exposure is less than 1 s.

In an embodiment, a ratio between a skin contact surface of the outer electrode and the skin contact surface of the inner electrode is greater than 2 and preferably greater than 10. In this way, there will be no discomfort by undesired heating in portions of the skin present beneath the outer electrode.

In an embodiment, a minimum distance between an outer edge of the inner electrode and an inner edge of the outer electrode is greater than 0.1 mm, more preferably greater than 0.2 mm. In a further embodiment, said minimum distance between the outer edge of the inner electrode and the inner edge of the outer electrode is smaller than 3 mm. There is no strict technical upper limit to said minimum distance (also referred to as gap between the inner and the outer electrodes), but for practical reasons to enable sufficient density of lesions from a grid of electrodes, for skin rejuvenation applications the gap should be smaller than 3 mm.

In an embodiment, the device comprises a plurality of inner electrodes and a plurality of outer electrodes, each of the plurality of outer electrodes surrounding a respective one of the plurality of inner electrodes. In this embodiment, at least some of the plurality of outer electrodes may be electrically connected to each other. In a preferred embodiment, the at least some of the plurality of outer electrodes may border each other so as to form a lattice structure. These embodiments require less wiring from the RF generator to the outer electrodes. Furthermore, more electrodes can be arranged on the same surface as compared to separate outer electrodes.

According to a second aspect, the invention relates to the use of the device as described above in the treatment of skin. The device may be used for therapeutic or non-therapeutic (e.g. cosmetic) treatment. The device is especially useful for rejuvenation of the skin, but may also be used for skin tightening.

Further preferred embodiments of the device and method according to the invention are described in the appended claims, disclosure of which is incorporated herein by reference.

BRIEF DESCRIPTION OF THE DRAWINGS

These and other aspects of the invention will be apparent from and elucidated further with reference to the embodiments described by way of example in the following description and with reference to the accompanying drawings, in which

FIGS. 2A-2G show examples of possible alternative embodiments of the inner electrode and the outer electrode;

The figures are purely diagrammatic and not drawn to scale. In the Figures, elements which correspond to elements already described may have the same reference numerals.

DETAILED DESCRIPTION OF EMBODIMENTS

Figure 1A:
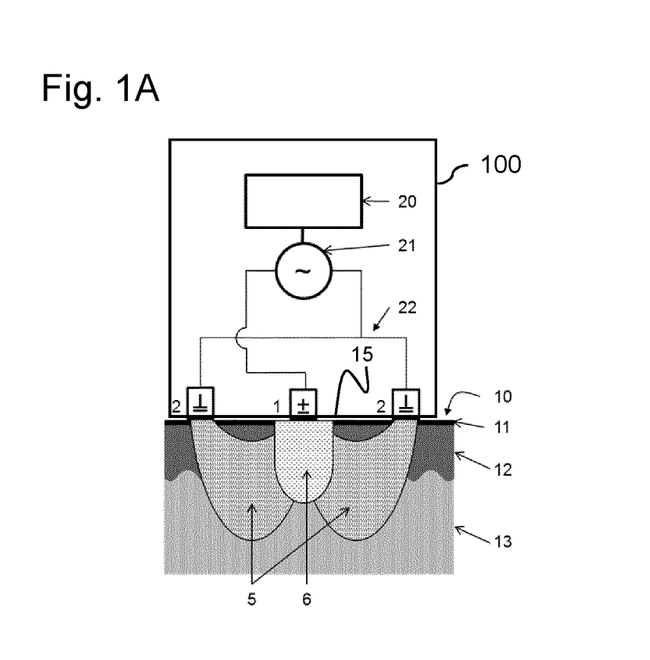
FIG. 1A is a schematic cross section of a device for skin treatment according to an embodiment of the present invention.

FIG. 1A is a schematic cross section of a device 100 for skin treatment according to an embodiment of the present invention. In this exemplary embodiment, the device 100 comprises an inner electrode 1 and an annular (ring-shaped) outer electrode 2 surrounding the inner electrode 1. The device 100 also comprises an electronic controller 20, and a radio frequency (RF) generator 21 connected by wiring 22 to the electrodes 1 and 2. In this Figure, the electrodes 1, 2 are shown in a position on a skin surface 10 consisting of the stratum corneum 11, epidermis 12 and dermis 13. When powered, the electrodes 1, 2 create electric field lines 5 within the skin and, due to the applied voltage in combination with the skin impedance, heat is deposited within the skin, thereby creating a non-ablative lesion 6, when the local skin temperature reaches a level above 65° C. and stays under 100° C. The electronic controller 20 may be arranged to control the RF generator 21. The RF generator 21 will provide a treatment voltage lower than 50 V. In some embodiments, the treatment voltage may even be lower than 40 V. The electronic controller 20 may comprise an impedance detection system to measure skin impedance between the electrodes 1, 2, and a feedback controller based on the measured skin impedance. The electronic controller 20 may further comprise a feedback adjuster for adjusting the applied voltage or applied pulse duration.

Figure 1B:
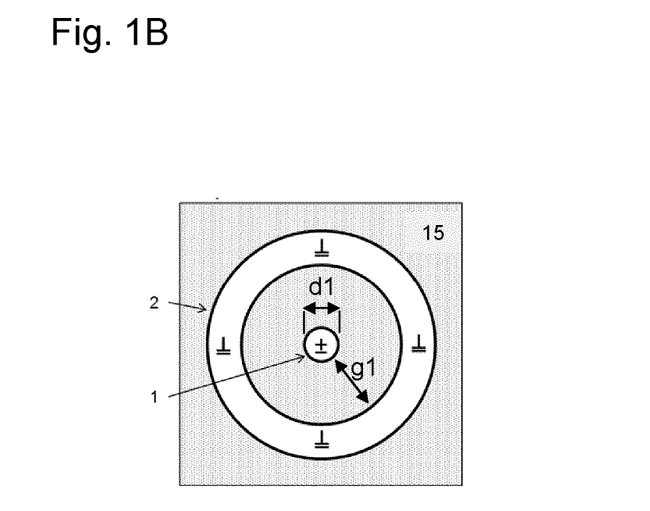
FIG. 1B shows a view of an operational side of the electrode configuration of the device of FIG. 1A.

FIG. 1B shows a top view of the electrode configuration of the device 100 shown in FIG. 1A, which is arranged on an operational side 15 of the device 100. The electrode configuration comprises the inner electrode 1 which is surrounded by the annular (ring-shaped) outer electrode 2. The inner electrode 1 is arranged at the center of the outer electrode 2. The specific electrode configuration of FIG. 1B comprising the inner electrode 1 and the surrounding annular outer electrode 2 is called a centrosymmetric electrode configuration. A skin contact surface of the inner electrode 1 is flat and has a diameter $d_1$ in a range of 200-500 µm. A minimum distance between an outer edge of the inner electrode and an inner edge of the outer electrode is referred to as gap $g_1$. More particularly, the gap $g_1$ is defined as the minimum distance between a point on the outer edge of the inner electrode 1 and a point on the inner edge of the outer electrode 2. In an embodiment, the gap $g_1$ is greater than 0.1 mm, preferably greater than 0.2 mm. Practical values for the gap $g_1$ lie below 3 mm.

Figure 2A:
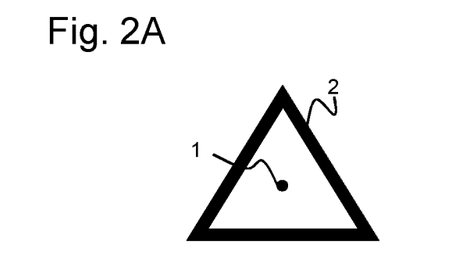
FIGS. 2A-2C show examples of possible alternative embodiments of the inner electrode and the outer electrode.
Figure 2B:
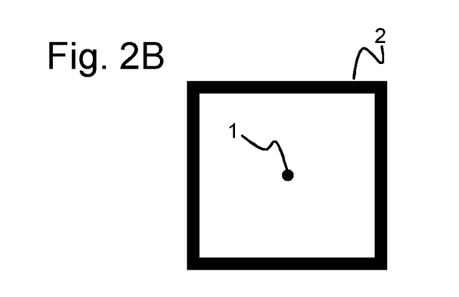
Figure 2C:
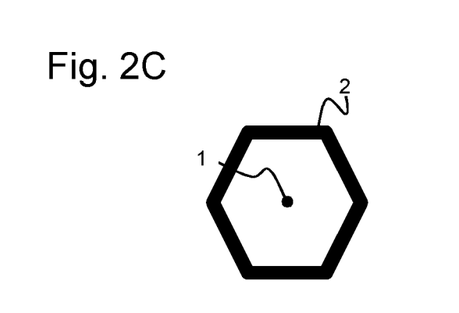
Figure 2D:
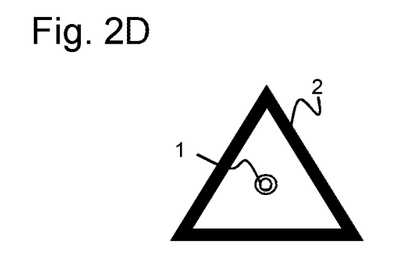
Figure 2E:
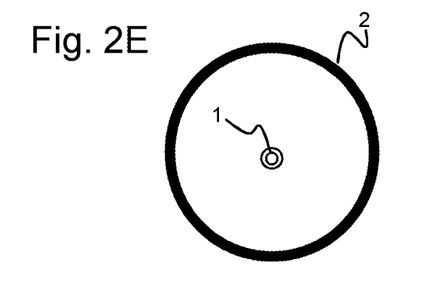
Figure 2F:
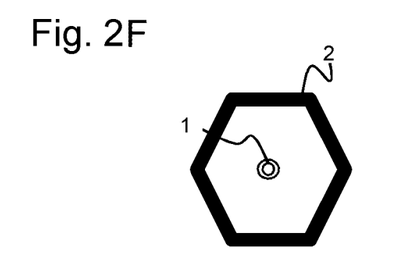
Figure 2G:
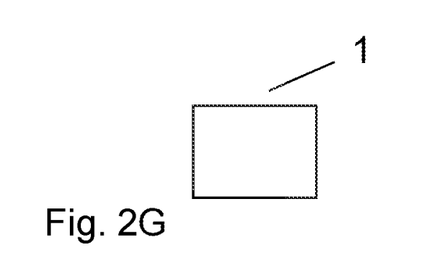

FIGS. 2A-2G show examples of alternative embodiments of the inner electrode 1 having a circular or disc shape and the outer electrode 2. FIG. 2A shows an equilateral triangular-shaped outer electrode 2. FIG. 2B shows a square-shaped outer electrode 2. FIG. 2C shows an equilateral polygonal outer electrode 2 having a honeycomb shape. FIG. 2D shows an equilateral triangular-shaped outer electrode 2 and an annular inner electrode 1. FIG. 2E shows a circular-shaped outer electrode 2 and an annular inner electrode 1. FIG. 2F shows an equilateral polygonal outer electrode 2 having a honeycomb shape and an annular inner electrode 1. FIG. 2G shows an inner electrode 1 having a square shape.

It is noted that in most embodiments the inner electrode 1 will be the active electrode (i.e. the electrode connected to the live wire), while the outer electrode 2 is the return electrode, but this could be the other way round.

To create multiple lesions concurrently, the device may comprise a plurality of inner electrodes, wherein each inner electrode is surrounded by a respective one of a plurality of outer electrodes. FIGS. 3A-3E show embodiments wherein the device comprises a plurality of inner electrodes 31 and a plurality of surrounding outer electrodes 32. Each of the plurality of outer electrodes 32 surrounds a respective one of the plurality of inner electrodes 31. The outer electrodes 32 may border each other so as to form a lattice structure as shown in the examples of FIGS. 3A and 3C-3E, or they may just be electrically coupled as shown in the example of FIG. 3B. This will require less wiring from the RF generator to the outer electrodes. Furthermore, more electrodes can be arranged on the same surface as compared to separate outer electrodes.

Figure 3A:
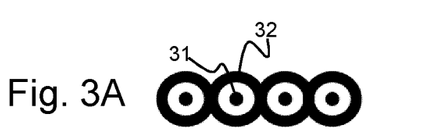
FIGS. 3A-3E show embodiments wherein the device comprises a plurality of inner electrodes and a plurality of surrounding outer electrodes.
Figure 3B:
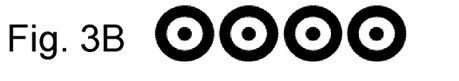
Figure 3C:
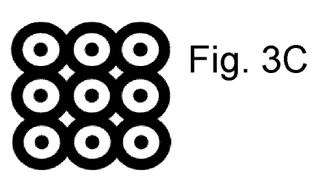
Figure 3D:
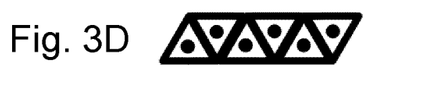
Figure 3E:
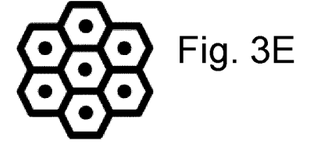

FIG. 3A shows a linear array of coupled centrosymmetric round electrode pairs. FIG. 3B shows a linear array of non-coupled centrosymmetric round electrode pairs. FIG. 3C shows a two-dimensional array of coupled centrosymmetric round electrode pairs. FIG. 3D shows a linear array of coupled centrosymmetric equilateral triangular electrode pairs, and FIG. 3E shows a two-dimensional array of coupled centrosymmetric honeycomb electrode pairs.

By arranging a plurality of inner electrodes 31 on the operational side 15 of the device 100 and surrounding each by an outer electrode 32, a larger skin surface can be treated at one time as compared to devices that comprise only one electrode pair.

Figure 4:
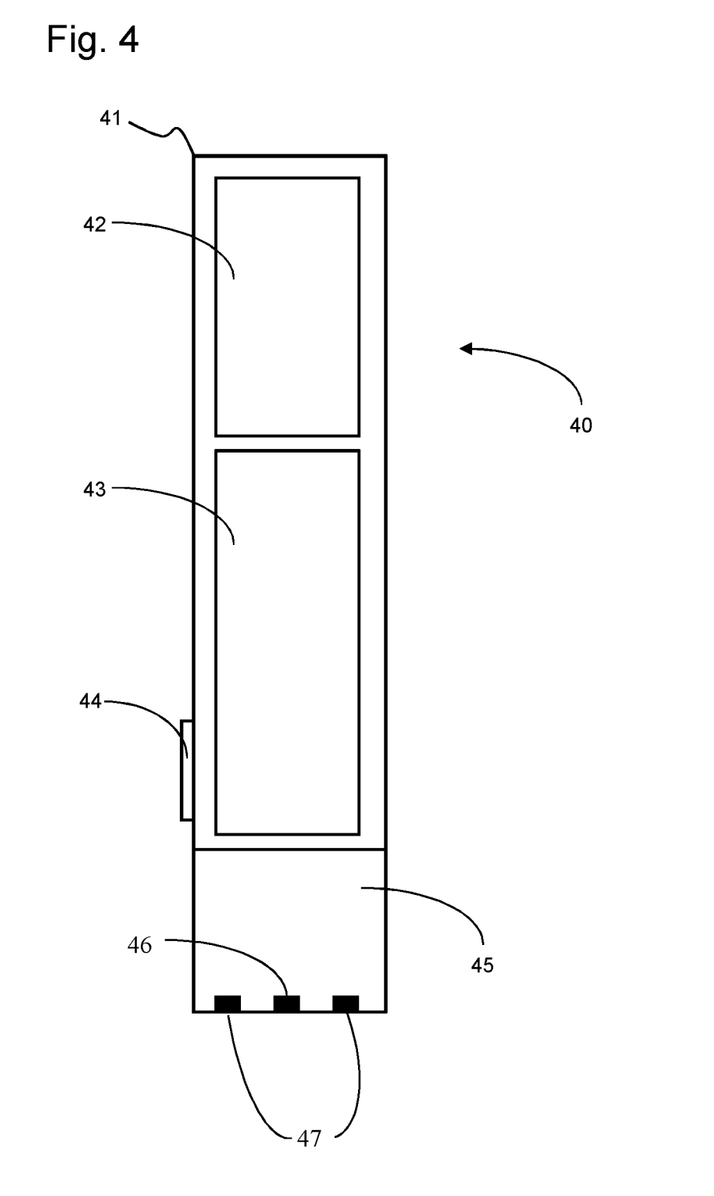
FIG. 4 schematically shows a device for skin treatment according to an embodiment of the present invention.

FIG. 4 schematically shows a device for skin treatment 40 according to another embodiment of the invention. The device 40 comprises a housing 41, a battery 42 and an electronic module 43. The electronic module 43 may comprise a PCB containing sensors, an RF generator, a feedback controller, and a function generator.

At the bottom, the device 40 comprises an inner electrode 46 and an outer electrode 47 provided on an operational side 45 of the device 40. The inner electrode 46 and the outer electrode 47 may be configured as described above. The device 40 also comprises a button 44 that can be activated in order to provide pulses of RF energy between the inner and outer electrodes 46, 47.

The device 40 has an elongated shape which, when suitably dimensioned, can be used like a pen which can be brought into contact with the skin. This embodiment is especially useful as a home-use handheld skin treatment device for skin rejuvenation.

In an embodiment, a ratio between the skin contact surface of the outer electrode 47 and the skin contact surface of the inner electrode 46 is greater than 2, and preferably greater than 10.

The device described above was tested by performing ex-vivo experiments. These ex-vivo experiments have shown robust lesion creation at voltages of 40V or less, and the impedance variations within both ex-vivo and in-vivo skin models investigated are within the +/−25% range.

Figure 5A:
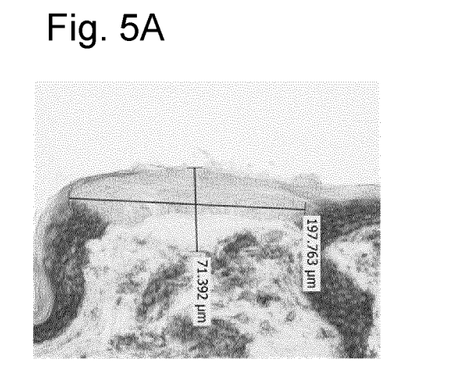
Figure 5B:
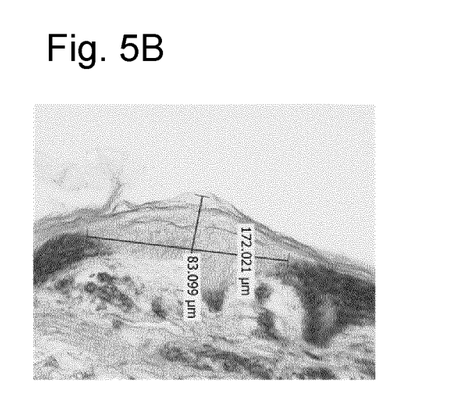
Figure 5C:
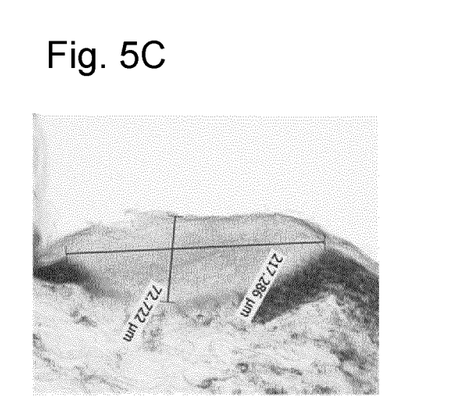

FIGS. 5A-5C show three examples of histological sections of lesions created in an ex-vivo skin sample by NTBC (Nitro blue tetrazolium chloride) staining, demonstrating the area of cell damage within the epidermis and collagen coagulation within the dermis of the skin. The treatment RF voltage was set to 39V and the application time of the treatment RF voltage was 50 ms. A diameter of the inner electrode was 0.2 mm, while the annular outer electrode had an inner diameter of 1.5 mm. The gap between the outer edge of the inner electrode and the inner edge of the outer electrode was equal to 0.65 mm. The thickness of the outer electrode was 2 mm.

The invention also relates to the use of the device according to the embodiments described above for RF treatment of skin. The device is especially useful for rejuvenation of the skin.

When using the device for RF skin treatment, a contact gel may be used, preferably a conductive gel, to improve the local skin impedance and the electrical contact between the skin and the device.

It is noted that in this document the word 'comprising' does not exclude the presence of elements or steps other than those listed, and the word 'a' or 'an' preceding an element does not exclude the presence of a plurality of such elements, and it is also noted that any reference signs do not limit the scope of the claims. Further, the invention is not limited to the embodiments, and the invention lies in each and every novel feature or combination of features described above or recited in mutually different dependent claims.

The invention claimed is:

1. A device for RF skin treatment of a skin comprising:
   an outer electrode arranged on an operational side of the device;
   an inner electrode arranged on the operational side of the device and surrounded by the outer electrode;
   an RF generator configured to supply an RF treatment voltage between the inner electrode and the outer electrode; and
   a controller configured to control the RF generator to generate the RF treatment voltage,
   wherein the controller is not configured to detect contact between the skin and the outer and inner electrodes,
   wherein the inner electrode is annular shaped and the outer electrode has an equilateral polygonal shape having one of three and six sides,
   wherein the inner electrode comprises a plurality of inner electrodes and the outer electrode comprises a plurality of outer electrodes, each of the plurality of outer electrodes surrounding a respective one of the plurality of inner electrodes.

2. The device according to claim 1, wherein a skin contact surface of the inner electrode has a largest dimension a range of one of 200-500 μm and 200-400 μm.

3. The device according to claim 1, wherein a diameter of the inner electrode is 0.2 mm, a gap between an outer edge of the inner electrode and an inner edge of the outer electrode is 0.65 mm, a thickness of the outer electrode is 2 mm, and wherein the controller is configured to control the RF generator to provide warming of the skin for effective cell damage within epidermis of the skin and collagen coagulation within dermis of the skin by generating the RF treatment voltage for 50 ms at 36 volts.

4. The device according to claim 1, wherein a ratio between a skin contact surface area of the outer electrode and a skin contact surface area of the inner electrode is greater than 2.

5. The device according to claim 1, wherein a minimum distance between an outer edge of the inner electrode and an inner edge of the outer electrode is greater than 0.1 mm.

6. The device according to claim 5, wherein the minimum distance between the outer edge of the inner electrode and the inner edge of the outer electrode is smaller than 3 mm.

7. The device according to claim 1, wherein the controller includes an impedance detection system configured to measure skin impedance between the outer and inner electrodes, and the controller is configured to maintain a local skin temperature at a target temperature by controlling the RF generator to adjust the RF treatment voltage based on the measured skin impedance.

8. The device according to claim 7, wherein the target temperature is above 65° C. and under 100° C.

9. The device according to claim 1, wherein at least some of the plurality of outer electrodes are electrically connected to each other.

10. The device according to claim 9, wherein the at least some of the plurality of outer electrodes border each other so as to form a lattice structure.

11. The device of claim 1, wherein a ratio between a skin contact surface area of the outer electrode and a skin contact surface area of the inner electrode is greater than 10.

12. The device of claim 1, wherein a minimum distance between an outer edge of the inner electrode and an inner edge of the outer electrode is greater than 0.2 mm.

13. A device for RF skin treatment comprising:
an outer electrode arranged on an operational side of the device;
an inner electrode arranged on the operational side of the device at a center of the outer electrode and surrounded by the outer electrode;
an RF generator arranged to supply an RF treatment voltage between the inner electrode and the outer electrode; and
a controller configured to control the RF generator to generate the RF treatment voltage,
wherein the controller is not configured to detect contact between the skin and the outer and inner electrodes, and
wherein the inner electrode is annular shaped and the outer electrode has an equilateral polygonal shape having one of three and six sides, and
wherein the inner electrode comprises a plurality of inner electrodes and the outer electrode comprises a plurality of outer electrodes, each of the plurality of outer electrodes surrounding a respective one of the plurality of inner electrodes.

14. The device of claim 13, wherein a skin contact surface of the inner electrode has a largest dimension in a range of 200-500 μm, and wherein the RF treatment voltage is less than 50 V and the target temperature is above 65° C. and under 100° C.

15. The device of claim 13, wherein the controller includes an impedance detection system configured to measure skin impedance between the outer and inner electrodes, and wherein the controller is configured to control the RF generator to generate the RF treatment voltage and maintain a local skin temperature at a target temperature by adjusting the RF treatment voltage based on the measured skin impedance.

16. A device for RF skin treatment comprising:
an outer electrode located on an operational side of the device;
an inner electrode located on the operational side of the device surrounded by the outer electrode;
an RF generator configured to supply an RF treatment voltage between the inner electrode and the outer electrode; and
a controller configured to control the RF generator to generate the RF treatment voltage without,
wherein the controller is not configured to detect contact between the skin and the outer and inner electrodes, and
wherein the inner electrode is square shaped and the outer electrode has an equilateral polygonal shape having one of three and six sides, and
wherein the inner electrode comprises a plurality of inner electrodes and the outer electrode comprises a plurality of outer electrodes, each of the plurality of outer electrodes surrounding a respective one of the plurality of inner electrodes.

17. The device of claim 16, wherein the controller includes an impedance detection system configured to measure skin impedance between the outer and inner electrodes, and the controller is configured to maintain a local skin temperature at a target temperature by controlling the RF generator to adjust the RF treatment voltage based on the measured skin impedance.

18. The device of claim 16, wherein the RF treatment voltage is less than 50 V and the target temperature is above 65° C. and under 100° C.

19. The device of claim 16, wherein a minimum distance between an outer edge of the inner electrode and an inner edge of the outer electrode is between 0.1 mm and 3 mm.

* * * * *